United States Patent [19]

Takata et al.

[11] Patent Number: 5,620,681
[45] Date of Patent: Apr. 15, 1997

[54] SELF-TANNING COSMETIC COMPOSITION

[75] Inventors: Sadaki Takata; Kenzo Ito, both of Yokohama, Japan

[73] Assignee: Shiseido Co., Ltd., Tokyo, Japan

[21] Appl. No.: 436,470

[22] PCT Filed: Jan. 7, 1994

[86] PCT No.: PCT/JP94/00016

§ 371 Date: May 26, 1995

§ 102(e) Date: May 26, 1995

[87] PCT Pub. No.: WO95/08980

PCT Pub. Date: Apr. 6, 1995

[30] Foreign Application Priority Data

Sep. 30, 1993 [JP] Japan .................. 5-268169
Sep. 30, 1993 [JP] Japan .................. 5-268170

[51] Int. Cl.$^6$ .............. A61K 7/42; A61K 31/74
[52] U.S. Cl. .............. 424/59; 424/60; 424/78.08
[58] Field of Search ................ 424/59, 60, 78.08

[56] References Cited

U.S. PATENT DOCUMENTS 5,232,688  8/1993  Ziegler et al. .............. 424/59
5,271,930  12/1993  Walele et al. .............. 424/78.08
5,302,378  4/1994  Crotty et al. .............. 424/59

FOREIGN PATENT DOCUMENTS

0425324A1  8/1990  European Pat. Off. .
0456545A1  4/1991  European Pat. Off. .
0547864A1  6/1993  European Pat. Off. .
WO91/122222  1/1991  WIPO .
WO9316683  9/1993  WIPO .
WO9422418  10/1994  WIPO .

OTHER PUBLICATIONS

Manufacturing Chemist & Aerosol News, Aug. 1976, p. 41, 'artificial suntan preparations'; p. 41, right column.

*Primary Examiner*—Shelly A. Dodson
*Attorney, Agent, or Firm*—Townsend & Banta

[57] ABSTRACT

A self-tanning cosmetic composition containing dihydroxy acetone and a polyoxyethylene-polyoxypropylene block polymer type surfactant. The oil content is less than 10%. A self-tanning cosmetic gel containing dihydroxy acetone, water, alcohol, a water-soluble cellulose type thickening agent and/or xanthane gum and a chelating agent is also disclosed. This cosmetic composition produces a good feeling when applied to the skin and uneven coloration is adequately prevented.

15 Claims, No Drawings

SELF-TANNING COSMETIC COMPOSITION

TECHNICAL FIELD

The present invention relates to a self-tanning cosmetic composition and, more particularly, to an improvement of a self-tanning cosmetic composition containing dihydroxy acetone.

BACKGROUND ART

A self-tanning cosmetic composition containing dihydroxy acetone (hereinunder referred to as "DHA" is intended to color the skin as if it were tanned without being exposed to the sun (ultraviolet), and various products are commercially available.

Those products are required to be uniformly applied to the skin in order to prevent uneven coloring. They are generally produced in the form of an emulsified product such as cream with the stability of the product containing DHA taken into consideration.

On the other hand, since a self-tanning cosmetic composition which does not contain oil can color the skin in a shorter time, a prescription of a lotion which does not contain oil and is mixed with DHA is proposed with importance set on a coloring ability to the skin.

However, since such a lotion does not spread well on the skin, uniform application is difficult, which results in uneven coloring of the skin. In other words, the finish in self-tanning is apt to be greatly damaged.

In addition, an aqueous self-tanning lotion has such a low viscosity that it often drips and causes unevenness in the color when it is applied to the skin. That is, since there is a great problem in the finish in self-tanning, the commercialization of the aqueous lotion is difficult.

In order to eliminate the problem in a self-tanning lotion such as dripping and uneven coloration, attempts have long been made to add a thickening agent to a self-tanning lotion so as to increase the viscosity.

For example, a method of adding a thickening agent which is represented by sodium polyacrylate (Carbopole 940, Carbopole 941, etc. produced by B.F.GOODRICH) to a prescription containing DHA has been investigated. However, this produces a great problem in the guarantee of the quality, because, for example, the stability of the viscosity with time is greatly lowered due to the decrease in the pH caused by the addition of DHA, and the external color of the product changes to brown with time.

In contrast, it is possible to prevent the color of a self-tanning lotion from changing to brown by using a nonionic thickening agent. In this case, however, it is also impossible to suppress the lowering of the viscosity with time. In addition, since the thickening effect of a nonionic thickening agent is much lower than that of a polyacrylate thickening agent, it is necessary to add a large amount of nonionic thickening agent to obtain the same viscosity. In this case, the product becomes tacky, which is peculiar to a polymer and produces an unpleasant feeling when applied to the skin.

DISCLOSURE OF INVENTION

Accordingly, it is a first object of the present invention to eliminate the above-described problems in the related art and to provide a self-tanning cosmetic which spreads well on the skin.

It is a second object of the present invention to provide a self-tanning cosmetic which can prevent dripping and uneven coloration, which produces a satisfactory feeling when applied to the skin, and which has an excellent quality stability with time.

As a result of studies undertaken by the present inventors so as to achieve the first object, it has been found that a self-tanning cosmetic composition produced by adding DHA and a specific surfactant to a base having a low oil content can color the skin beautifully without a fear of uneven coloring. On the basis of this finding, the present invention has been completed.

A self-tanning cosmetic composition provided in a first aspect of the present invention is characterized in that the oil content is less than 10%, and in that it contains DHA and a polyoxyethylene-polyoxypropylene block copolymer type surfactant.

To achieve the second object, it is necessary to add alcohol and a chelate as well as a specific water-soluble thickening agent.

A self-tanning cosmetic gel provided in a second aspect of the present invention comprises DHA, water, alcohol, a water-soluble cellulose thickening agent and/or xanthane gum and a chelate.

BEST MODE FOR CARRYING OUT THE INVENTION

The structure of the present invention will be described in detail.

DHA used in the present invention is generally used in a self-tanning cosmetic composition and the amount of DHA used is generally about 1 to 10 wt % of the total amount of self-tanning cosmetic composition with due consideration of the coloring effect thereof to the skin.

The base applicable to the present invention is an aqueous base containing substantially no oil or an emulsion base having a low oil content. In the case of an emulsion base, the oil content is less than 10%, preferably less than 5%.

If an emulsion base contains not less than 10% of oil, a self-tanning cosmetic composition which spreads well on the skin is obtained in the related art, but it takes sometimes longer to color the skin with the cosmetic.

On the other hand, a self-tanning cosmetic produced from the base containing substantially no oil can color the skin with high clarity and a beautiful appearance.

As examples of the polyoxyethylene-polyoxypropylene block copolymer surfactant used in the present invention will be cited commercially available Pluronic and Tetronic (trade names: produced by Asahi Denka Kogyo K.K., BASF).

There are different grades of these surfactants in accordance with the number of moles of polyoxyethylene, and polyoxypropylene added but the grade of the surfactant used in the present invention is not specially restricted so long as the surfactant is soluble to the base.

The amount of polyoxyethylene-polyoxypropylene block copolymer surfactant added is 0.1 to 3 wt %, preferably 0.5 to 2 wt % of the total amount of self-tanning cosmetic composition. If the amount of polyoxyethylene-polyoxypropylene block copolymer surfactant added is less than 1 wt %, it is impossible to improve the spreadability of the cosmetic to the skin. In order to improve the spreadability of the cosmetic to the skin, addition of 3 wt % of polyoxyethylene-polyoxypropylene block copolymer suffices and further addition is not necessary.

As examples of the water-soluble cellulose thickening agent used in the self-tanning cosmetic gel of the present invention, methyl cellulose, hydroxypropyl cellulose hydroxypropylmethyl cellulose, hydroxypropylemethyl cellulose, and hydroxyethyl cellulose will be cited, but it is not restricted thereto so long as the thickening agent is a nonionic cellulose thickening agent. The nonionic cellulose thickening agent is appropriately selected in accordance with the object. The amount of water-soluble cellulose thickening agent added to a self-tanning cosmetic gel of the present invention is 0.1 to 2 wt %, preferably 0.5 to 1 wt % of the total amount of cosmetic composition. If it is less than 0.1 wt %, the thickening effect is low, so that it is impossible to effectively prevent dripping and uneven coloration. On the other hand, if the amount exceeds 2 wt %, the cosmetic becomes tacky, which is peculiar to a polymer, and produces an unpleasant feeling when applied to the skin. If a xanthane gum is used together within the above-described range, it is possible to further improve the stability of viscosity with time.

The alcohol used in the present invention is mainly ethanol. The amount of alcohol added is 5 to 40 wt %, preferably 10 to 30 wt %, more preferably 20 to 30 wt % of the total amount of cosmetic composition. If the alcohol is less than 5 wt %, it is difficult to stabilize the viscosity by the cellulose type thickening agent used in the present invention.

On the other hand, addition of more than 40% of alcohol has a possibility of coagulating the thickening agent.

Examples of the chelating agent used in the present invention are edetates (ethylenediaminetetraacetates) and sodium hexametaphosphate. The amount of chelating agent added is preferably 0.01 to 0.3 wt % of the total amount of self-tanning cosmetic gel. If it is less than 0.01 wt %, it is insufficient that the suppression of the lowering of the viscosity of the cosmetic composition with time. On the other hand, not only that the addition of more than 0.3 wt % of chelating agent is unnecessary from the point of view of the suppression of the lowering of the viscosity, but also the increase in the salt content produces a fear of lowering the stability of the cosmetic composition with time.

It is possible to add humectant, surfactant, ultraviolet absorber, drugs, coloring agent, powder, perfume, etc. to a self-tanning cosmetic composition of the present invention in the range which does not damage the effects and the quality of the present invention.

The present invention will be explained in more detail with reference to the following examples. However, the present invention is not restricted to the following examples. The amount of each ingredient represents wt % so long as not specified otherwise.

EXAMPLE 1

Self-Tanning Lotion

Prescription

| Part A | |
|---|---|
| Ethyl alcohol | 5.0 % |
| Vitamin E acetate | 0.05 |
| POE (60) hardened castor oil | 1.0 |
| 2-hydroxy-4-methoxybenzophenone | 0.2 |

-continued

| Paraben | 0.2 |
|---|---|
| Perfume | 0.02 |
| Part B | |
| Dihydroxy acetone | 5.0 |
| dl-α-tocopherol 2-L-diester potassium Ascorbic phosphate | 0.1 |
| Glycerin | 2.0 |
| 1,3-butylene glycol | 2.0 |
| Pullonic L-62 (produced by Asahi Denka Kogyo K.K.) | 1.0 |
| Xanthane gum | 0.2 |
| Disodium edetate | 0.1 |
| Ion-exchanged water | balance |

Preparation Process

In the part B, disodium edetate and DHA were dissolved in the Ion-exchanged water, and xanthane gum which moistened with glycerin and 1,3-butylene glycol were added. Each ingredient of the part A was sufficiently dissolved and added to the part B, thereby obtaining a self-tanning lotion.

Effect test

The self-tanning lotion obtained in Example 1 was applied to the right arm of an examinee and the self-tanning lotion produced in the same way as in Example 1 except for not using Pullonic L-62 (Comparative Example 1) was applied to the left arm of the examinee. The spreadability of each self-tanning lotion to the skin and the colored state were evaluated by 20 examinees in accordance with the following criteria. The results are shown in Table 1.

Spreadability
○: Very good
Δ: Good
×: Bad
Colored state
○: Evenly colored
Δ: Slightly uneven
×: Uneven

TABLE 1

| | | Ex. 1 (Number of examinees) | Comp..1 |
|---|---|---|---|
| Spreadability | ○ | 15 | 5 |
| | Δ | 4 | 11 |
| | X | 1 | 4 |
| Colored state | ○ | 17 | 3 |
| | Δ | 3 | 12 |
| | X | 0 | 5 |

As is clear from Table 1, the self-tanning lotion in Example 1 shows excellent spreadability and colored state in spite of the small oil content.

EXAMPLE 2

Self-Tanning Emulsion

Prescription

| Part A | |
|---|---|
| Squalane | 2.0 |
| POE (60) glycerylmonoisostearate | 1.0 |
| Glycerylmonostearate | 1.0 |
| Butyl paraben | 0.2 |
| Perfume | 0.1 |

-continued

| Part B | |
|---|---|
| 1,3-butylene glycol | 5.0 |
| Dehydroxy acetone (DHA) | 3.0 |
| Pullonic L-64 (produced by Asahi Denka Kogyo K.K.) | 2.0 |
| Hydroxyethyl cellulose | 0.2 |
| Sodium citrate | 0.1 |
| Sodium hexametaphosphate | 0.1 |
| Ion-exchanged water | balance |

Preparation Process

In the part B, sodium citrate, sodium hexametaphosphate and DHA were dissolved in the Ion-exchanged water, and Pullonic L-62 was added thereto and the mixture was completely dissolved. Hydroxyethyl cellulose moistened with 1,3-butylene glycol was added and the mixture was heated. Each ingredient of the part A was sufficiently dissolved, heated and added to the part B for the purpose of emulsification.

The self-tanning cosmetic in each of Examples 1 and 2 colors the skin in a short time, easily spreads to the skin and is unlikely to cause uneven coloring.

EXAMPLE 3

Self-Tanning Gel

Prescription

| Part A | |
|---|---|
| Ethanol | 30.0 % |
| Pullonic L-64 | 1.0 |
| Perfume | 0.1 |
| Paraben | 0.1 |
| Vitamin E acetate | 0.01 |
| Part B | |
| 1,3-butylene glycol | 5.0 |
| DHA | 3.0 |
| Hydroxypropyl cellulose | 0.4 |
| Xanthane gum | 0.2 |
| Chelating agent(Disodium edetate) | 0.05 |
| Ion-exchanged water | balance |

Preparation Process

Dissolved part A was added to the dissolved part B, and the mixture was adequately stirred so as to obtain a self-tanning gel.

Effect test

The type and the amount of chelate and the amount of alcohol were varied in the prescription in Example 3 (the change in the amount was adjusted by the amount of Ion-exchanged water), and the viscosity and the stability of color tone of the product with time were examined.

A sample was filled in a bottle and allowed to stand at 50° C. for 1 month. The viscosity reduction ratio was measured by a B-type viscometer and a change in the color tone was visually estimated.

Criteria for estimation of a change in the color tone
○: No change was observed.
Δ: A slight change was observed.
×: Browning was observed (colored).

The results are shown in Table 2.

TABLE 2

| | Chelating agent | Viscosity reduction ratio (%) | Browning |
|---|---|---|---|
| Comp. 2 | None | 95 | ○ |
| Ex. 3 | Disodium Edetate | 10 | ○ |
| Ex. 4 | Edetic Acid (EDTA) | 40 | ○ |
| Ex. 5 | Trisodium Edetate | 10 | ○ to Δ |
| Ex. 6 | Tetrasodium Edetate | 11 | Δ |
| Ex. 7 | Triethanolamine Edetate | 15 | ○ |
| Ex. 8 | Sodium hexametaphosphate | 11 | ○ |

It is understood from Table 2 that although a self-tanning gel composed of DHA, alcohol, water-soluble cellulose thickening agent and xanthane gum can suppress a color change, the reduction in the viscosity with time is very large if no chelating agent is added. In other words, the reduction in the viscosity is not suppressed until addition of a chelate.

Table 3, shows the relationship between the amount of chelate added and the viscosity reduction ratio.

TABLE 3

| | Chelate | Viscosity reduction ratio (%) |
|---|---|---|
| Comp. 2 | 0 | 95 |
| Ex. 9 | 0.005 | 60 |
| Ex. 10 | 0.01 | 20 |
| Ex. 11 | 0.05 | 15 |
| Ex. 12 | 0.1 | 12 |
| Ex. 13 | 0.3 | 8 |
| Ex. 14 | 0.5 | 8 |

In Table 3, Disodium edetate was used as a chelating agent.

As is clear from Table 3, when no chelate is added, the viscosity reduction ratio is very large. It is greatly suppressed by the addition of a chelate, and the stability is increased in proportion to the amount of chelate added so long as the amount is not more than 0.3%.

In the prescription containing 0.008% of disodium edetate as a chelating agent, the relationship between the amount of ethanol added and the viscosity reduction ratio was examined. The results are shown in Table 4.

TABLE 4

| | Effect of ethanol contents | | |
|---|---|---|---|
| | Ethanol | Initial viscosity ratio (cps) | Viscosity reduction |
| Comp. 3 | 0 | 818 | 62 |
| Ex. 15 | 10 | 1414 | 60 |
| Ex. 16 | 20 | 1550 | 49 |
| Ex. 17 | 30 | 1837 | 45 |
| Ex. 18 | 50 | 2245 | 66 |

As is clear from Table 4, the addition of ethanol increases the initial viscosity, and when the amount of ethanol added is in the range of 20 to 30%, the viscosity reduction with time is greatly suppressed.

As explained above, since the self-tanning cosmetic gel according to the present invention contains substantially no oil, the skin coloring speed is very fast. Furthermore, since the base has an appropriate viscosity, it is possible to spread uniformly to the skin unlike to the liquid lotion, so that uneven coloring is prevented and it produces a pleasant feeling when it is applied to the skin.

We claim:

1. A self-tanning cosmetic composition comprising: dihydroxy acetone, a polyoxyethylene-polyoxypropylene block copolymer surfactant, and less than 10% by weight of oil.

2. A self-tanning cosmetic composition according to claim 1, wherein the content of said polyoxyethylene-polyoxypropylene block copolymer type surfactant is 0.1 to 3 wt %.

3. A self-tanning cosmetic gel comprising: dihydroxy acetone; water; alcohol; a water-soluble non ionic cellulose thickening agent; and a chelating agent.

4. A self-tanning cosmetic gel according to claim 3, wherein said alcohol is ethanol.

5. A self-tanning cosmetic gel according to claim 3, wherein the content of said alcohol is 5 to 40 wt %.

6. A self-tanning cosmetic gel according to claim 3, wherein the content of said alcohol is 10 to 30 wt %.

7. A self-tanning cosmetic gel according to claim 3, wherein the content of said alcohol is 20 to 30 wt %.

8. A self-tanning cosmetic gel according to claim 3, wherein said chelating agent is an edetate.

9. A self-tanning cosmetic gel according to claim 3, wherein the content of said chelating agent is 0.01 to 0.3 wt %.

10. A self-tanning cosmetic gel according to claim 3, wherein the content of said water-soluble cellulose thickening agent is 0.1 to 2 wt %.

11. A self-tanning cosmetic gel according to claim 3, further comprising xanthane gum.

12. A self-tanning cosmetic gel according to claim 3, wherein said cosmetic gel is a transparent self-tanning cosmetic gel which contains substantially no oil.

13. A self-tanning cosmetic composition comprising: from 1–10 wt % of dihydroxy acetone, from 0.1–3 wt % of a polyoxyethylene-polyoxypropylene block polymer surfactant, and wherein the composition contains from substantially no oil to less than 10% of oil.

14. A self-tanning cosmetic composition comprising: dihydroxy acetone, from about 5–40 wt % of alcohol, from 0.1–2 wt % of a non-ionic cellulose thickening agent, water, and from about 0.01–0.3 wt % of a chelating agent selected from the group consisting of edetates and sodium hexametaphosphate.

15. The self-tanning cosmetic composition of claim 14, further comprising from 1–3 wt % of a polyoxyethylene-polyoxypropylene block copolymer surfactant.

* * * * *